(12) United States Patent
Otsubo et al.

(10) Patent No.: US 8,758,318 B2
(45) Date of Patent: Jun. 24, 2014

(54) PULL-ON ARTICLE

(75) Inventors: Toshifumi Otsubo, Kagawa (JP); Tatsuya Hashimoto, Kagawa (JP); Shinichi Ishikawa, Kagawa (JP); Jun Okuda, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 449 days.

(21) Appl. No.: 13/140,127

(22) PCT Filed: Dec. 25, 2009

(86) PCT No.: PCT/JP2009/007292
§ 371 (c)(1),
(2), (4) Date: Jun. 16, 2011

(87) PCT Pub. No.: WO2010/073717
PCT Pub. Date: Jul. 1, 2010

(65) Prior Publication Data
US 2012/0035564 A1 Feb. 9, 2012

(30) Foreign Application Priority Data
Dec. 25, 2008 (JP) .................. 2008-331378

(51) Int. Cl.
*A61F 13/494* (2006.01)
*A61F 13/496* (2006.01)

(52) U.S. Cl.
USPC .................. 604/385.25; 604/385.24

(58) Field of Classification Search
USPC .................. 604/370, 385.25, 385.24
See application file for complete search history.

(56) References Cited

U.S. PATENT DOCUMENTS

| 4,515,854 | A | * | 5/1985 | Kogame et al. ............ 442/329 |
| 4,641,381 | A | | 2/1987 | Heran et al. |
| 5,690,626 | A | * | 11/1997 | Suzuki et al. ............ 604/385.25 |
| 2003/0199843 | A1 | * | 10/2003 | Kato et al. .............. 604/385.3 |
| 2006/0025746 | A1 | | 2/2006 | Sasaki et al. |
| 2007/0034315 | A1 | * | 2/2007 | Sandin et al. ............ 156/73.1 |
| 2008/0124995 | A1 | * | 5/2008 | Mitsuno et al. ............ 442/329 |
| 2008/0125738 | A1 | | 5/2008 | Tsuji et al. |

FOREIGN PATENT DOCUMENTS

| JP | 61-207605 A | 9/1986 |
| JP | 10-052458 A | 2/1998 |
| JP | 2001-522703 A | 11/2001 |

(Continued)

OTHER PUBLICATIONS

International Search Report for PCT/JP2009/007292 mailed Apr. 6, 2010.

*Primary Examiner* — Susan Su
(74) *Attorney, Agent, or Firm* — Lowe Hauptman & Ham LLP

(57) ABSTRACT

A pull-on article comprises a chassis including a first waist region, a second waist region and a crotch region between the first and second waist regions. The article is shaped into a pull-on having a waist and a pair of leg openings by weld-bonding side edges of the first and second waist regions. The waist and leg openings are respectively provided along respective edged defining the waist and leg openings with waist and leg elastic members which are respectively formed into a tape shape having a relatively width dimension. The first and second waist regions, and the leg and waist elastic members are respectively formed of a fibrous non-woven fabric including at least thermoplastic fibers wherein the leg and waist elastic members include at least elastically extendible fibers as the thermoplastic fibers.

15 Claims, 2 Drawing Sheets

(56) References Cited

FOREIGN PATENT DOCUMENTS

| | | | |
|---|---|---|---|
| JP | 3090821 | U | 12/2002 |
| JP | 2003-024383 | A | 1/2003 |
| JP | 2005-287699 | A | 10/2005 |
| JP | 2006-061680 | A | 3/2006 |
| WO | 2008066007 | A1 | 5/2008 |

\* cited by examiner

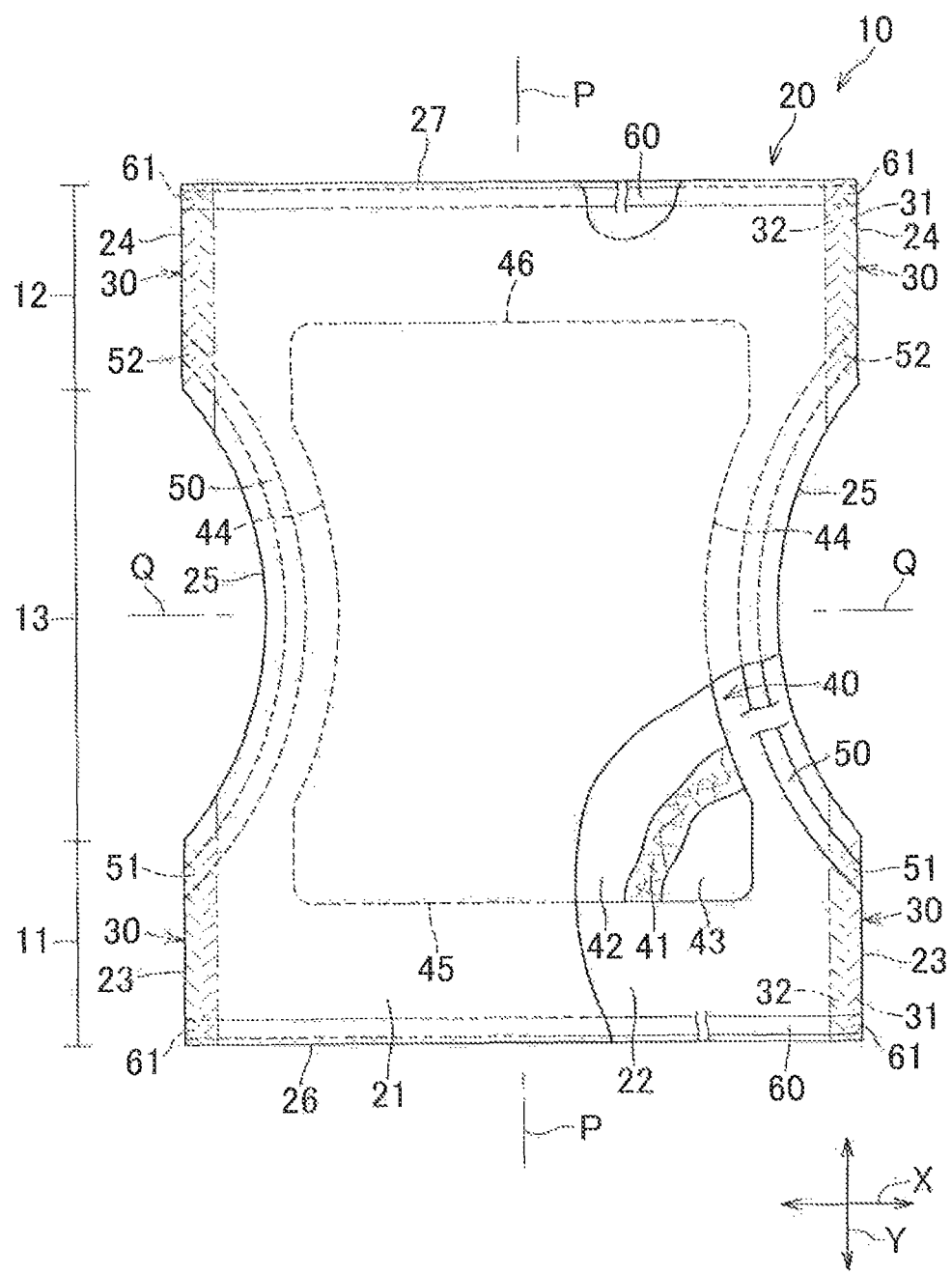

PULL-ON ARTICLE

RELATED APPLICATIONS

The present application is a National Phase of International Application Number PCT/JP2009/0007292, filed Dec. 25, 2009, which claims priority from, Japanese Application Number 2008-331378, filed Dec. 25, 2008.

TECHNICAL FIELD

The present disclosure relates generally to pull-on articles and, particularly, to pull-on articles such as disposable diapers, toilet training pants, incontinent briefs and the like.

BACKGROUND

Pull-on articles are known, for example, from JP 2001-522703 W, to have a waist opening and a pair of leg openings wherein front and rear waist regions of an absorbent chassis are weld-bonded thereby to obtain a three-dimensional article, i.e., a pull-on article or a pant type article. According to most of known pull-on articles, including the pull-on article disclosed in JP 2001-522703 W, an outer cover comprises a front waist region, a rear waist region and a crotch region between the front and rear waist regions. Opposite side edges of the front waist region are weld-boned with opposite side edges of the rear waist region. The waist-opening and the leg-openings are respectively provided with strand-like elastic members made from rubber material so that edges defining these openings may be put in close contact with the wearer's body. These elastic members have ends overlapping the welded seams and weld-bonded concurrently with the outer cover to prevent the elastic members from falling out.

After the article has been used, the welded seams may be burst to pull the front and rear waist regions apart from each other and the article may be taken off from the wearer in order to prevent body waste from clinging to the wearer's legs or the other regions. To burst the welded seams, the wearer or a helper may hold the front and rear waist regions with the wearer's or the helper's both hands and pull them outward in opposite directions. The respective welded seams are burst in a vicinity of the waist-opening as the front and rear waist regions are pulled apart. However, in vicinities of the leg-openings remote from the waist opening held by the wearer's or the helper's both hands, the welded seams are not well burst. Rather, the outer cover forming the front and rear waist regions is irregularly ruptured inside the welded seams as viewed in a transverse direction. Such rupture may prevent the welded seams from smoothly bursting.

Additionally, even after the outer cover has been ruptured, leg and waist elastic members, particularly the latter, remain firmly weld-bonded to the respective welded seams and do not readily fall out from the associated welded seams. However, if the side edges of the front and rear waist regions are further pulled apart in opposite directions, the leg elastic members will be further extended between the ruptured outer cover and the associated welded seams until the leg elastic members fallout from the associated welded seams. Thereupon the wearer's or the helper's both hands may be uncomfortably whipped with the leg elastic members which snap-back.

The inventors have contemplated several reasons why the known articles have the problems described above. A partial reason is that the known article has a great difference in elongation-at-break (%) between the outer cover and the leg and waist elastic members. Specifically, an elongation-at-break of the outer cover is about 40-60%, whereas an elongation-at-break of the leg and waist elastic members is at least 400% because the strand-elastic members are formed of rubber material having relatively great elongation-at-break. Another partial reason is that if the waist-opening is held and forcibly pulled apart in opposite directions, the pulling speed is gradually accelerated toward the leg-openings which are remote from the waist-opening. Such tensile force exerted at a high velocity seems to get involved in ruptures of the outer cover rather than in bursting of the welded seams.

It is one object of one or more embodiments of the present invention to provide a pull-on article that the wearer's and the helper's hands are not uncomfortably whipped with leg and waist elastic members when welded seams of side edges of front and rear waist regions are burst during taking off the article.

It is another object of one or more embodiments of the present invention is to provide a pull-on article which does not create a feeling of discomfort pressure against the wearer's thighs and waist region and provide a good sealing about the wearer's thighs and waist region thereby to effectively prevent body waste discharged from the wearer leaking outward from leg and waist opening edges.

It is a further object of one or more embodiments of the present invention is to provide a pull-on article which provides leg and waist elastic members for effectively sealing over relatively wide regions about the wearer's thighs and waist region.

It is an additional object of one or more embodiments of the present invention to provide a pull-on article in which leg and waist elastic members are rupturable in vicinities of welded seams where the elastic members are attached to the first and second waist regions, when welded seams of side edges of first and second waist regions are burst and thereby the side edges of the first and second waist regions are smoothly separated from each other in opposite directions.

SUMMARY

One or more embodiments of the invention relates to a pull-on article which comprises a chassis including a first waist region, a second waist region and a crotch region between the first and second waist regions. The crotch region is provided along its edges of a pair of leg openings with leg elastic members formed into a band shape. The first and second waist regions are also provided along its edges defining a waist opening with waist elastic members formed into a band shape. The first and second waist regions have side edges thereof weld-bonded to define the welded seams. The first and second waist regions, and the leg and waist elastic members are respectively formed of a fibrous non-woven fabric including at least thermoplastic fibers wherein the leg and waist elastic members include at least elastically extendible fibers as the thermoplastic fibers. The welded seams of the first and second waist regions may be burst therealong by the wearer's or the helper's hands during taking off the article from the wearer.

Preferably, the leg and waist elastic members have a width dimension of at least 15, the first and second waist regions, and the leg and waist elastic member have respectively a basis mass of at least 15 g/m$^2$ wherein an elongation (%) at break of the leg and waist elastic members is less than three times that of the first and second waist regions.

One or more embodiments of the invention relates to a pull-on article having a longitudinal direction and a transverse direction orthogonal to the longitudinal direction. The article comprises a chassis of a fibrous material and including, in the longitudinal direction, opposite first and second waist regions and a crotch region in between. Transversely opposite side edges of the waist regions are intermittently bonded together in the longitudinal direction at welded seams to define a waist opening and two leg openings. The article further comprises at least one band of an elasticized non-woven fabric attached to the chassis along a periphery of at least one of the waist and leg openings to define at least one respective waist or leg elastic member. The elasticized non-woven fabric at end portions of the elastic member is intermittently bonded together with the fibrous material of the chassis at at least one of the welded seams. An elongation-at-break of the elasticized non-woven fabric of the elastic member is less than three times that of the fibrous material of the chassis in the first and second waist regions.

One or more embodiments of the invention relates to a pull-on article having a longitudinal direction and a transverse direction orthogonal to the longitudinal direction. The article comprises a chassis of a fibrous material and including, in the longitudinal direction, opposite first and second waist regions and a crotch region in between. Transversely opposite side edges of the waist regions are intermittently bonded together in the longitudinal direction at welded seams to define a waist opening and two leg openings. The article further comprises at least one band of an elasticized non-woven fabric attached to the chassis along a periphery of at least one of the waist and leg openings to define at least one respective waist or leg elastic member. The elasticized non-woven fabric at end portions of the elastic member is intermittently bonded together with the fibrous material of the chassis at at least one of the welded seams. The elasticized non-woven fabric in a vicinity of the at least one welded seam is rupturable in response to a pulling force sufficient to separate the first and second waist regions from each other, thereby facilitating smooth separation of the first and second waist regions from each other when the article is to be removed from a wearer after use.

BRIEF DESCRIPTION OF DRAWINGS

FIG. 1 is a perspective view of a pull-on diaper as a waist opening and leg openings are opened and partially broken for convenience of depiction.
[FIG. 2]
FIG. 2 is a plan view of the diaper as developed and flattened and partially broken for convenience of depiction.

BEST MODE FOR CARRYING OUT THE INVENTION

Figure 1:
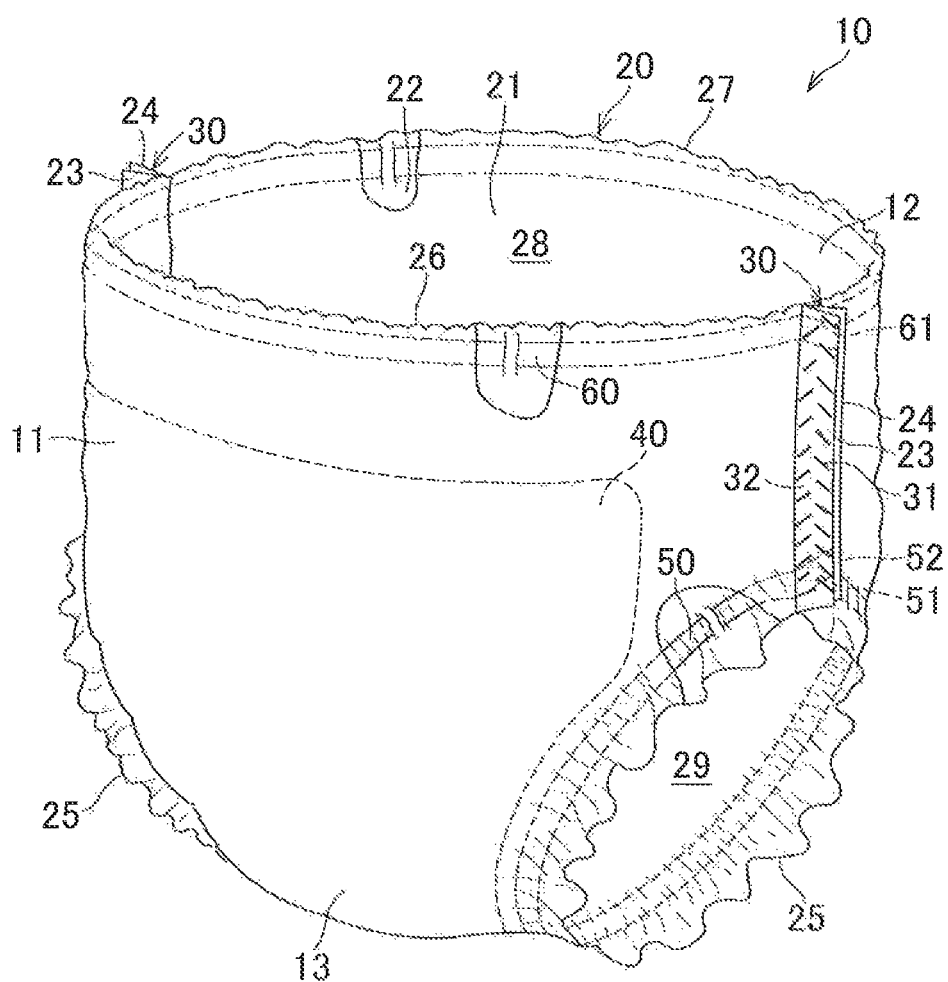
[FIG. 1]

Details of exemplary embodiments will be more fully understood from the following description of a pull-on disposable diaper given hereunder with reference to the accompanying drawings in which a longitudinal direction of the article is indicated by Y and a transverse direction orthogonal to the longitudinal direction Y is indicated by X.

Referring now to FIGS. 1 and 2, the diaper 10 according to this exemplary embodiment is of the so-called pull-on type. The diaper 10 comprises a chassis 20 including a front waist region 11, a rear waist region 12 and a crotch region 13 between the front and rear waist regions 11, 12.

The chassis 20 further includes a bodyside liner 21 defining a bodyside surface and an outer cover 22 defining a non-bodyside surface. The chassis 20 is contoured by side edges 23 of the front waist region 11, side edges 24 of the rear waist region 12 and side edges 25 of the crotch region 13, respectively opposed in the transverse direction X, and end edges 26, 27 of the front and rear waist regions 11, 12 opposed in the longitudinal direction Y.

The article 10 further comprises a liquid-absorbent structure 40 which is interposed between the bodyside liner 21 and the outer cover 22. The liquid-absorbent structure 40 comprises a liquid-absorbent core 41, a liquid-dispersant sheet 42 covering the core 41 and a leakage barrier 43 interposed between the liquid-dispersant sheet 42 and the outer cover 22. The liquid-absorbent structure 40 extends at least across the crotch region 13 and preferably further extends into the front and rear waist regions 11, 12 in the longitudinal direction Y.

The liquid-absorbent structure 40 is contoured by transversely opposite side edges 44 and longitudinally opposed front and rear ends 45, 46 wherein the opposed side edges 44 in the crotch region 13 are concave toward a longitudinal center line P-P so as to reduce a width dimension of the structure 40 in the transverse direction X. The width dimension reduced in this manner assures that the liquid-absorbent structure 40 is brought into a good fit with the wearer's crotch without becoming bulky. The bodyside liner 21 and the outer cover 22 extend outward in the transverse direction X beyond the side edges 44 of the liquid-absorbent structure 40. A pair of leg elastic members 50 are respectively formed each as a band, and interposed between the bodyside liner 21 and the outer cover 22 in respective regions thereof extending outward beyond the side edges 44. The bodyside liner 21 and the outer cover 22 extend outward also in the longitudinal direction Y beyond the front and rear ends 45 of the liquid-absorbent structure 40. Waist elastic members 60 are also each as a band and interposed between the bodyside liner 21 and the outer cover 22 in respective regions thereof extending outward beyond the front and rear ends 45.

Whilst, in the present embodiment, an absorbent structure is provided it may be omitted or, alternatively, it may take different forms.

Moreover, the waist elastic members may be omitted; or may take an alternative form, for example, they may be a different shape or have different elastic properties to the leg elastic members.

The leg elastic members 50 and the waist elastic members 60 are respectively formed of an elasticized fibrous non-woven fabric at least including thermoplastic fibers. Specifically, the leg elastic members 50 and the waist elastic members 60 respectively comprise non-elastically extendible fibers such as, for example, polyolefin fibers such as polyethylene fibers, polypropylene fibers and a mixture fibers of polyethylene and polypropylene and elastically extendible fibers such as, for example, polyurethane fiber both being thermoplastic and mixed together at a ratio of 1:1 in basis mass (g/m$^2$) to provide fibrous non-woven fabrics having a basis mass of about 15-40 g/m$^2$, preferably about 35 g/m$^2$. As a result, the fibrous non-woven fabric is extendible despite including the non-elastically extendible fibers. It should be noted here that the term "non-elastically extendible" means that the non-woven fabric is extendible by being plastically deformed in its length direction by its extension. The fibrous non-woven fabric is then subjected to a well-known gear extension process so that the non-elastically extendible fibers are non-elastically extended. In the gear extension process, the fibrous non-woven fabric is passed between a pair of gears engaging with each other and rotating. It is preferable to use a pair of gears which are engageable with each other so that cogs' tops of one of the gears are spaced apart from ditches' bottoms of the other. It should be noted here that since the non-woven fabric includes a sufficient quantity of non-elastically extendible fibers not having rubber properties, it gives the wearer a cloth-like touch.

The respective leg elastic members 50 are contractibly attached under tension to the chassis 20 along the associated side edges 25 of the crotch region 13 by means of adhesive. More specifically, the leg elastic members 50 extend, in a concave shape, gradually toward the longitudinal center line P-P as the leg members 50 get closer to a transverse center line Q-Q from front and rear ends 51, 52. It should be appreciated here that the respective front ends 51 of the leg elastic members 50 are present in the front waist region 11 and the respective rear ends 52 of the leg elastic members 50 are present in the rear waist region 12. Each of the leg elastic members 50 has a width dimension of about 15-30 mm, preferably about 20 mm, at least in vicinities of the front and rear ends 51, 52. The leg elastic members 50 configured in the manner as has been described above assure that the side edges 25 of the crotch region 13 can be put in close contact with the wearer's thighs and thereby leakage of body fluids such as urine can be reliably prevented.

The waist elastic members 60 are contractibly attached to the chassis 20 under tension in the transverse direction X along the front and rear ends 26, 27 of the chassis 20 by means of adhesive. Opposite ends 61 of the waist elastic member 60 extending along the front end 26 of the chassis 20 are present on the respective side edges 23 of the front waist region 11 and opposite ends 61, 61 of the waist elastic member 60 extending along the rear end 27 of the chassis 20 are present on the respective side edges 24 of the rear waist region 24. Each of the waist elastic members 60 has a width dimension of about 15-30 mm, preferably about 20 mm, at least in vicinities of the opposite ends 61.

In the diaper 10 as has been described above, the front waist region 11 and the rear waist region 12 are weld-bonded together along the side edges 23,24 of the front and rear waist regions 11,12 to define respective welded seams 30 and to shape the diaper 10 into a pull-on type or a pant type diaper. Thereupon the front end 26 cooperates with the rear end 27 to define a waist-opening 28 and the side edges 25 of the crotch region 13 define respective leg-openings 29.

The welded seams 30 may be formed, for example, by well-known ultrasonic welding techniques and each of the welded seams 30 comprises a plurality of welded portions 31 in which the bodyside liner 21 and the outer cover 22 are weld-bonded together and a plurality of non-welded regions 32 in which these liner and cover 21, 22 are not weld-bonded together. The welded portions 31 are intermittently arranged in the longitudinally direction Y, specifically, the welded portions 31 and non-welded portions 32 alternately arranged in the longitudinal direction Y. More specifically, the welded regions 31 are arranged in two rows in the longitudinal direction Y so that the welded portion 31 and the non-welded portion 32 alternate not only in the longitudinal direction Y but also in the transverse direction X. The longitudinally opposite ends 51, 52 of the respective leg elastic members 50 and the transversely opposite ends 61 of the respective waist elastic members 60 are present on the side edges 23 of the front waist region 11 and the side edges 24 of the rear waist region 12 along which the welded seams 30 are formed. Preferably, the ends 51, 52 of the respective leg elastic members 50 and the transversely opposite ends 61 of the respective waist elastic members 60 are weld-bonded together with the side edges 23, 24 of the respective waist regions 11, 12. Each of zones in which the respective ends 51, 52, 61 of the leg elastic members 50 and the waist elastic members 60 overlap the welded seams 30 includes at least one welded portion 31 and at least one non-welded portion 32.

The welded seams 30, the welded portions 31 and the non-welded portions 32 are indicated by imaginary lines for convenience of depiction in FIG. 2 so as to correspond to those in FIG. 1.

When it is desired to take off the diaper 10 from the wearer, the welded seams 30 formed along the side edges 23, 24 of the front and rear waist regions 11, 12 may be burst to separate the front and rear waist regions 11, 12 from each other in order to prevent body waste from clinging to the wearer's legs.

To burst the welded seams 30, the front waist region 11 and the rear waist region 12 may be pulled apart from each other with the front waist region 11 pinched by the wearer' or the helper's fingers of one hand in vicinities of the side edges 23 along the associated seams 30 as viewed in the transverse direction X and with the rear waist region 12 pinched by the fingers of the other hand in vicinities of the side edges 24 along the associated welded seams 30 as viewed in the transverse direction X. Then, with the front and rear ends 26, 27 of the chassis 20 defining the waist-opening 28 pinched by the fingers of the respective hands, the front and rear ends 26, 27 may be pulled down toward the leg openings 29. As has previously been described, the waist elastic members 60 are attached to the chassis 20 along the end edges 26,27 by means of adhesive and further the opposite ends 61 of the respective waist elastic members 60 are weld-bonded together with the bodyside liner 21 and the outer cover 22 by the respective welded seams 30. In the similar manner, the leg elastic members 50 are attached to the chassis 20 along the respective side edges 25 by means of adhesive and further the respective leg elastic members 50 are weld-bonded together with the bodyside liner 21 and the outer cover 22 by the respectively welded seams 30.

The leg elastic members 50 and the waist elastic members 60 are respectively formed of the fibrous non-woven fabric including thermoplastic fibers and therefore the elastic members 50, 60 are well welded to the bodyside liner 21 and the outer cover 22 formed of thermoplastic fibers (except elastically extendible fibers) similar to the leg and waist elastic member. The elastic members 50, 60 have a basis mass of about 15-40 g/m$^2$, preferably about 35 g/m$^2$. The elastic members 50, 60 respectively formed into the shape of a band.

Each of at least the segments of the leg elastic members 50 and the waist elastic members 60 overlapping the respective welded seams 30 has a width dimension of about 15-30 mm, preferably about 20 mm substantially larger than the case in which the strand-like elastic members are used.

The front and rear waist regions 11, 12 may be pulled apart from each other about the respective welded seams 30 to separate the bodyside liner 21 and the outer cover 22 and the leg and waist elastic members 50, 60 one from another and thereby the respective welded seams 30 are burst therealong. Thus it is possible to prevent the leg and waist elastic members 50, 60 from being exclusively extended and the wearer's or the helper's hands from being uncomfortably whipped with these elastic members 50, 60 upon snap-backing thereof.

In order to effectively prevent such whipping, it is preferable that an elongation-at-break (%) of each of the elastic members is less than about three times that of the front and rear waist regions. Specifically, it is preferable that the former is 100-200% and the latter is 40-60%.

The elongation-at-break values (%) were derived from measurements of tensile tests according to JIS L 19130(1998).

However, the following measurement conditions were set.
Width dimension of sample: 25 mm
Tension rate: 100 mm/min
Distance between chucks: 100 mm It should be noted here an elongation-at-break of each of leg and waist elastic members as well as of front and waist regions of some diapers which are on the market in Japan were as follows:

| | |
|---|---|
| Leg elastic members | 400-500% |
| Front and rear waist regions | 40-60% |

The leg and waist elastic members 50, 60 are formed of fibers and, therefore, even if the bodyside liner 21 and the outer cover 22 are ruptured as the welded seams 30 are burst, the leg and waist elastic members 50, 60 follow ruptures of the bodyside liner 21 and the outer cover 22 to be disentangled and thereby to be pulled apart in the transverse direction X. Particularly, the leg and waist elastic members 50, 60 include welded portion(s) 31 and the non-welded portion(s) 32 so that the fibers in the non-welded portion 32 may be pulled apart in opposite directions around the welded portion 31 serving as the rigid and non-breakable point and thereby the fibers of the leg and waist elastic members may be untangled around the welded portion 31. In contrast, if the welded portion is continuously formed in the longitudinal direction Y and none of the non-weld portions 32 are formed, the fibers of the leg and waist elastic members will not be easily pulled apart and the elastic members will not be easily ruptured because no portion serving as the basic points around which the fibers can be untangled is present.

Furthermore, the elasticized fibrous non-woven fabrics forming the leg and waist elastic members 50, 60 have been subjected to the extension process described previously and, thereby, the non-elastically extendible fibers in the leg and waist elastic members 50, 60 are partially diameter-reduced so as to be easily disentangled. Disentanglement of the fibers facilitates the fibrous non-woven fabric to be ruptured.

While the waist elastic members 60 are depicted herein to be provided in vicinities of the front and rear ends 26, 27 of the chassis 20, the elastic members 60 may be additionally provided in the crotch region 13 also so that the front and rear waist regions 11, 12 can be put in close contact with the wearer's entire waist. The width dimension of the leg and waist elastic members 50, 60 should be understood to be exemplarily indicated dimension. The width dimension depends on whether the article is made exclusively for adult or for baby. Even in the same classification of the article for adult or for baby, the width dimension in question depends on the production size and the most suitable width dimension may be appropriately selected within the respective classifications.

While the chassis 20 is depicted herein to be formed of the bodyside liner 21 and the outer cover 22, it is also possible to form the chassis 20 by one of these liner and cover. In this case, each of the leg and waist elastic members 50, 60 may be bonded to the chassis 20 only on one surface thereof. The leg and waist elastic members 50, 60 formed of the fibrous non-woven fabric allow the bond area to be larger than the case in which the strand-like elastic members are used and thereby allow the bond strength to be correspondingly increased. As a consequence, it is unnecessary to interposed the leg and waist elastic members 50, 60 between the bodyside liner 21 and the outer cover 22 and thereby to fix them to the chassis 20. It is further unnecessary to interpose these elastic members 50, 60 between the bodyside liner 21 and the outer cover 22 from another viewpoint. Specifically, since these elastic members 50, 60 are formed of the fibrous non-woven fabric, which includes thermoplastic fibers, and the elastic members 50, 60 are welded to bond to the chassis 20, the number of members as well as the number of the steps in the course of making the article can be advantageously reduced.

The longitudinally opposed ends 51, 52 of the leg elastic members 50 and the transversely opposite ends 61 of the waist elastic members 60 weld-bonded to the chassis 20 in the respective welded seams 30 respectively have the width dimension of at least 15 mm. Such dimensioning allows the bond area over which the leg and waist elastic members 50, 60 are weld-bonded to the bodyside liner 21 and the outer cover 22 to be effectively enlarged. Consequentially, during use of the article, it is possible to restrict the leg and waist elastic members 50, 60 from falling off the bodyside liner 21 and the outer cover 22.

While the welded portions 31 in the respective welded seams 30 are formed so as to be oblique with respect to the longitudinal center line P-P in the shown embodiment, the welded portions 31 may be orthogonal or parallel to the longitudinal center line P-P or formed in curved lines or dots.

While the bodyside liner 21 and the outer cover 22 cooperate with each other to form the front waist region 11, the rear waist region 12 and the crotch region 13 in the shown embodiment, it is possible to form the respective regions by independent units, i.e., a front waist unit, a rear waist unit and a crotch unit and then to connect these units to form the article. In this case, various arrangements such that the leg elastic members are not present in the crotch unit but present only in the front and rear waist units, or the elastic members provided in the crotch region serve also as the leg elastic members.

Materials for the bodyside liner 21 and the outer cover 22, as well as the leg and waist elastic members 50, 60, may be, for example, a spun bonded fibrous non-woven fabric, a fibrous non-woven fabric made of conjugate fibers such as spun bonded/melt blown/spun bonded (SMS) conjugate fibers, an air-through non-woven fabric, a melt bonded non-woven fabric, etc. as known in the relevant field of art. The fibrous non-woven fabrics for the leg and waist elastic members 50, 60 are mixed with elastically extendible fibers, as previously described. The barrier 43 may be formed, for example, of a moisture-permeable plastic film and the liquid-absorbent core 41 may be formed, for example, of the materials commonly used in the relevant field of art, for example, a mixture of fluff pulp and super-absorbent polymer particles, with, optionally, thermoplastic staple fibers. The welded seams 30 may be formed by supersonic techniques or heat sealing techniques commonly used in the relevant field of art.

The aspects of the present invention described above may be arranged in at least the following items:

(1) The pull-on article has the longitudinal direction Y and the transverse direction X orthogonal to the longitudinal direction, and comprises:

the chassis 20; the waist opening 28; and the pair of leg openings 29;
 the chassis including: the bodyside surface; the first waist region 11 having the first side edges 23 opposed in the transverse direction and the first end edge 26 between the first side edges, the first waist region being formed of the fibrous non-woven fabric including at least the thermoplastic fibers; the second waist region 12 having the second side edges 24 opposed in the transverse direction and the second end edge 27 between the second side edges as well as opposed to the first end edge 26 of the first waist region of the first waist region in the longitudinal direction, the second waist region being formed of the fibrous non-woven fabric including at least thermoplastic fibers; and the crotch region 13 between the first and second waist regions and having the third side edges 25 opposed in the transverse direction;

the waist opening 28 and the leg openings 29 being defined by weld-bonding the first and second side edges 23,24 intermittently in the longitudinal direction to define the welded seams 30; and the crotch region being provided along the third side edges with the leg elastic members 50 which are formed into a band shape and made of the elasticized fibrous non-woven fabric including at least thermoplastic fibers.

The aspect of the present invention described in the above item (1) may provide one or more of the following advantageous effects.

(a) The wearer's and the helper's hands are not uncomfortably whipped with the leg elastic members when the welded seams of the side edges of the front and rear waist regions are burst during taking off the article.

(b) The article does not create a feeling of discomfort pressure against the wearer' thighs and provides a good sealing about the wearer's thighs thereby to effectively prevent body waste discharged from the wearer leaking outward from the leg openings edges.

(c) The article provides the leg elastic members for effectively sealing over relatively wide regions about the wearer's thighs.

(d) The leg elastic members are rupturable in vicinities of welded seams where the elastic members are attached to the first and second waist regions, when the welded seams of side edges of the front and rear waist regions are burst and thereby the side edges are smoothly separated from each other in opposite directions.

Additionally, one or more of the following embodiments are provided in accordance with further aspects.

(2) The leg elastic members 50 have both ends 51,52 thereof in the longitudinal direction weld-bonded intermittently to the first and second side edges 23,24 to form parts of the welded seams.

(3) The leg elastic members 50 each has a width dimension of about 15-30 mm and a basic mass of 15-40 g/m².

(4) The elasticized fibrous non-woven fabric forming the leg elastic members 50 includes elastically extendible thermoplastic fibers and non-elastically extendible thermoplastic fibers as the thermoplastic fibers.

(5) The leg elastic members 50 are treated by the gear extending process wherein the fibrous non-woven fabric including the non-elastically extendible fibers are passed through between a pair of gears so that the non-elastically extendible thermoplastic fibers are extendible.

(6) The elongation-at-break (%) of the leg elastic members 50 is less than three times that of the first and second waist regions 11, 12.

(7) The elongation-at-break of the first and second waist regions 11, 12 is about 40-60% and the elongation-at-break of the leg elastic members 50 is about 100-200%.

(8) The leg elastic members 50 are located on the bodyside surface 21 of the chassis 20.

(9) The article further comprises the waist elastic members 60 provides along the first and second end edges 26,27 and formed of an elasticized fibrous non-woven fabric including at least thermoplastic fibers. An advantage of this embodiment is as follows:

(e) The waist elastic members are rupturable in vicinities of welded seams where the elastic members are attached to the first and second waist regions, when the welded seams of side edges of the front and rear waist regions are burst and thereby the side edges are smoothly separated from each other in opposite directions.

(10) The waist elastic members have both ends 51, 61; 52, thereof in the transverse direction weld-bonded intermittently to the first and second end edges to define parts of the welded seams.

(11) The waist elastic members 60 each has the width dimension of about 15-30 mm and a basis mass of 15-40 g/m².

(12) The elasticized fibrous non-woven fabric forming the waist elastic members includes elastically extendible thermoplastic fibers and non-elastically extendible thermoplastic fibers as the thermoplastic fibers.

(13) The waist elastic members are treated by the Gear extending process wherein the fibrous non-woven fabric are passed through between the pair of gears wherein the non-elastically extendible thermoplastic fibers are extended so that the fibrous non-woven fabric is easily extendible.

(14) The elongation-at-break (%) of the waist elastic members 60 is less than three times that of said first and second waist regions 11, 12.

(15) The elongation-at-break of the first and second waist regions 11, 12 is about 40-60% and the elongation-at-break of the waist elastic members 60 is about 100-200%.

(16) The waist elastic members are located on the bodyside surface 21 of the chassis 20.

(17) The article further comprises an absorbent structure 40 disposed on the bodyside surface 21 of the chassis 20.

(18) The absorbent structure 40 comprises an absorbent core 41 has at least an outer surface thereof covered with a liquid-permeable sheet 42.

According to the embodiments in the above (2)-(18), more than one of the advantageous effects set forth in (a)-(e) are better ensured. Further advantageous effects of the respective embodiments may be obtained as discussed in the respective related descriptions.

(19) The pull-on article 10 has a longitudinal direction Y and a transverse direction X orthogonal to the longitudinal direction, and comprises:

a chassis 20 of a fibrous material and including, in the longitudinal direction, opposite first and second waist regions 11, 12 and a crotch region 13 in between, wherein transversely opposite side edges 23, 24 of the waist regions are intermittently bonded together in the longitudinal direction at welded seams 30 to define a waist opening 28 and two leg openings 29; and at least one band 50, 60 of an elasticized non-woven fabric attached to the chassis along a periphery of at least one of the waist and leg openings to define at least one respective waist and leg elastic member;

wherein the elasticized non-woven fabric at end portions 51, 61 of the elastic member is intermittently bonded together with the fibrous material of the chassis at at least one of the welded seams; and an elongation-at-break of the elasticized non-woven fabric of the elastic member is less than three times that of the fibrous material of the chassis in the first and second waist regions.

The aspect of the present invention described in the above item (19) may provide one or more of the advantageous effects detailed at (a) through (e).

(20) The article is free of elastic strands along peripheries of the waist and leg openings. As a result, advantageous effects (a) and/or (e) are ensured.

(21) The pull-on article 10 has a longitudinal direction Y and a transverse direction X orthogonal to the longitudinal direction, and comprises:

a chassis 20 of a fibrous material and including, in the longitudinal direction, opposite first and second waist regions 11, 12 and a crotch region 13 in between, wherein transversely opposite side edges 23, 24 of the waist regions are intermittently bonded together in the longitudinal direction at welded seams 30 to define a waist opening 28 and two leg openings 29; and at least one band 50, 60 of an elasticized non-woven fabric attached to the chassis along a periphery of at least one of the waist and leg openings to define at least one respective waist or leg elastic member;

wherein the elasticized non-woven fabric at end portions 51, 61 of the elastic member is intermittently bonded together with the fibrous material of the chassis at at least one of the welded seams; and the elasticized non-woven fabric in a vicinity of the at least one welded seam is rupturable in response to a pulling force (not shown) sufficient to separate the first and second waist regions from each other, thereby facilitating smooth separation of the first and second waist regions from each other when the article is to be removed from a wearer after use, as discussed at (d). The advantageous effects disclosed at (a)-(c) and (e) are also obtainable.

The terms "first", "second" and "third" herein are used merely for distinguishing between similar elements. Furthermore, the wording "first waist region" herein means one of the front and rear waist regions, and the wording "second waist region" herein means the other.

The invention claimed is:

1. A pull-on article having a longitudinal direction and a transverse direction orthogonal to said longitudinal direction, said article comprising:
   a chassis;
   a pair of leg openings;
   said chassis including:
      a first waist region having first side edges opposed in said transverse direction and a first end edge between said first side edges, said first waist region being formed of a fibrous non-woven fabric including at least thermoplastic fibers;
      a second waist region having second side edges opposed in said transverse direction and a second end edge between said second side edges as well as opposed to said first end edge in said longitudinal direction, said second waist region being formed of said fibrous non-woven fabric including at least thermoplastic fibers; and
      a crotch region between said first and second waist region and having third side edges opposed in said transverse direction;
   said waist opening and said leg openings being defined by weld-bonding said first and second side edges intermittently in said longitudinal direction to form welded seams;
   said crotch region being provided along said third side edges with leg elastic members which are formed into a band shape and made of an elasticized fibrous non-woven fabric including at least thermoplastic fibers,
   wherein said elasticized fibrous non-woven fabric forming said leg elastic members includes elastically extendible thermoplastic fibers and non-elastically extendible thermoplastic fibers as said thermoplastic fibers.

2. The article according to claim 1, wherein said leg elastic members have both ends thereof in said longitudinal direction weld-bonded intermittently to said first and second side edges to define parts of said welded seams.

3. The article according to claim 1, wherein said leg elastic members each has a width dimension of about 15-30 mm and a basic mass of 15-40 g/m$^2$.

4. The article according to claim 1, wherein said leg elastic members are treated by a gear extending process wherein said fibrous non-woven fabric are passed through between a pair of gears so that said fibrous non-woven fabric including said non-elastically extendible fibers are extendible.

5. The article according to claim 1, wherein an elongation-at-break (%) of said leg elastic members is less than three times that of said first and second waist regions.

6. The article according to claim 5, wherein said elongation-at-break of said first and second waist regions is about 40-60% and said elongation-at-break of said leg elastic members is about 100-200%.

7. The article according to claim 1, further comprising waist elastic members provided along said first and second end edges and formed of an elasticized fibrous non-woven fabric including at least thermoplastic fibers.

8. The article according to claim 7, wherein said waist elastic members have both ends thereof in said transverse direction weld-bonded intermittently to said first and second end edges to define parts of said welded seams.

9. The article according to claim 7, wherein said waist elastic members each has a width dimension of about 15-30 mm and a basic mass of 15-40 g/m$^2$.

10. The article according to claim 7, wherein said elasticized fibrous non-woven fabric forming said waist elastic members includes elastically extendible thermoplastic fibers and non-elastically extendible thermoplastic fibers as said thermoplastic fibers.

11. The article according to claim 10, wherein said waist elastic members are treated by a gear extending process wherein said fibrous non-woven fabric are passed through between a pair of gears wherein said fibrous non-woven fabric including said non-elastically extendible thermoplastic fibers are extendible.

12. The article according to claim 7, wherein an elongation-at-break (%) of said waist elastic members is less than three times that of said first and second waist regions.

13. The article according to claim 12, wherein said elongation-at-break of said first and second waist regions is about 40-60% and said elongation-at-break of said waist elastic members is about 100-200%.

14. The article according claim 1, further comprises an absorbent structure which is disposed on a bodyside surface of said chassis.

15. The article according to claim 14, wherein said absorbent structure comprises an absorbent core that has at least an outer surface thereof covered with a liquid-permeable sheet.

* * * * *